United States Patent [19]
Ueshima et al.

[11] 3,956,355
[45] May 11, 1976

[54] METHOD FOR MANUFACTURING CYANONORBORNENE

[75] Inventors: Takashi Ueshima, Yokohama;
Tosiro Yokoyama, Kawasaki;
Shoichi Kobayashi, Yokohama, all of Japan

[73] Assignee: Showa Denko Kabushiki Kaisha, Tokyo, Japan

[22] Filed: Apr. 3, 1975

[21] Appl. No.: 564,819

[30] Foreign Application Priority Data
Apr. 9, 1974   Japan.............................. 49-39454

[52] U.S. Cl................................................. 260/464
[51] Int. Cl.²................ C07C 120/00; C07C 121/48
[58] Field of Search..................................... 260/464

[56] References Cited
UNITED STATES PATENTS

| | | |
|---|---|---|
| 3,304,167 | 2/1967 | Buntin et al................... 260/464 X |
| 3,470,248 | 9/1969 | Brotherton et al............ 260/464 X |
| 3,492,330 | 1/1970 | Trecker et al.................. 260/464 X |
| 3,784,581 | 1/1974 | Boyer.................................. 260/464 |

OTHER PUBLICATIONS

The Chemistry of Acrylonitrile, Cyanamid, 2nd Ed., p. 13, 1959.

*Primary Examiner*—Joseph Paul Brust
*Attorney, Agent, or Firm*—Kemon, Palmer & Estabrook

[57] ABSTRACT

A method for manufacturing cyanonorbornene by reacting acrylonitrile with a fraction resulting from cracking a petroleum fraction, particularly naphtha and mainly containing a mixture of various kinds of hydrocarbon each having five carbon atoms.

16 Claims, No Drawings

METHOD FOR MANUFACTURING CYANONORBORNENE

This invention relates to a method for manufacturing cyanonorbornene (5-cyano-bicyclo[2,2,1]-heptene-2) and more particularly to a method for manufacturing cyanonorbornene which consists in reacting acrylonitrile with a fraction (hereinafter referred to as "$C_5$ fraction") resulting from cracking a petroleum fraction and mainly containing a mixture of various kinds of hydrocarbon each having five carbon atoms.

Cyanonorbornene is a useful compound used as a raw material for manufacturing polymers. Already known is the cyanonorbornene-manufacturing method which is based on the Diels-Alder reaction between cyclopentadiene and acrylonitrile. Cyclopentadiene, one of the reactants, is contained in the low boiling fraction of coal tar as well as in coke oven gas. In recent years, however, cyclopentadiene is separated from the $C_5$ fraction produced in cracking a petroleum fraction, mainly naphtha. Cyclopentadiene thus obtained is a very reactive unstable material ready to be dimerized, for example, even at room temperature. Generally, cyclopentadiene is purposely dimerized into dicyclopentadiene for marketing. In practical application, however, said dimerized product is thermally cracked back to the original cyclopentadiene. Separation of cyclopentadiene from the $C_5$ fraction is essentially based on the fact that cyclopentadiene is readily dimerized under heat to form dicyclopentadiene whose boiling point is considerably different from those of the other components of the $C_5$ fraction. The process of said separation consists in first heating the $C_5$ fraction to dimerize cyclopentadiene and then distilling the heated liquid to separate high boiling dicyclopentadiene from the other components of the $C_5$ fraction in the form of bottom residue. The dicyclopentadiene thus separated, however, contains codimers whose boiling points approximate that of dicyclopentadiene, for example, codimers of cyclopentadiene and other dienes such as isoprene, thus failing to provide a high purity product. The customary method of obtaining pure cyclopentadiene basically utilizes the fact that dicyclopentadiene is more quickly depolymerized than impure codimers, and is carried out by further cracking of said impure dicyclopentadiene to provide a high purity product. This cracking is generally effected by any of the following known processes: (a) the atmospheric distillation process consisting of fractionating cyclopentadiene-bearing product obtained by cracking while thermally cracking dicyclopentadiene at a temperature of about 170°C; (b) the liquid phase cracking process consisting of introducing dicyclopentadiene into a high boiling solvent heated to 250° to 260°C for thermal cracking and then fractionating cyclopentadiene-bearing product obtained by said cracking; and (c) the gaseous phase cracking process at a high temperature of 260° to 350°C for a relatively short time. Though these processes can indeed thermally crack 70 to 90% of dicyclopentadiene into monomeric cyclopentadiene, residual part of the dicyclopentadiene tends to be turned into a higher polymeric form, reducing the yield of pure cyclopentadiene.

The present inventors previously developed a process of reacting easily procurable raw dicyclopentadiene with acrylonitrile without using the above-mentioned complicated and uneconomical cyclopentadiene separating processes and filed a patent application (Japanese Pat. application No. 91,782/72). However, demand has still been made for the realization of a simpler and more economical process for manufacturing cyanonorbornene.

This invention has been accomplished in view of the above-mentioned circumstances and is intended to provide a simple, economical, industrially advantageous method for manufacturing cyanonorbornene. The method of this invention is characterized by reacting acrylonitrile with the $C_5$ fraction resulting from cracking a petroleum fraction and mainly containing a mixture of various kinds of 5-carbon atom hydrocarbon, said $C_5$ fraction having a boiling point ranging from 15° to 55°C and containing at least 5% by weight of cyclopentadiene, at a temperature ranging between 0° and 150°C, with the molar ratio of acrylonitrile to cyclopentadiene contained in said $C_5$ fraction chosen to fall within the range from 0.3:1 to 3:1.

The above-mentioned method of this invention attains the selective reaction of acrylonitrile with the $C_5$ fraction without the previous separation of cyclopentadiene or dicyclopentadiene and can provide cyanonorbornene by a simple and economical process, thus offering a prominent industrial advantage.

The $C_5$ fraction, one of the starting materials of this invention, is separated from a mixture of multifarious hydrocarbons produced by cracking petroleum fractions, for example, heavy oil, light oil, kerosine, and preferably nephtha and mainly contains various kinds of 5-carbon atom hydrocarbons and has a boiling point ranging between 15° and 55°C. The composition of the $C_5$ fraction actually varies with the kind of a source petroleum fraction from which said $C_5$ fraction is derived and the conditions in which cracking is carried out and the components produced by cracking are separated from each other. The hydrocarbons contained in the general $C_5$ fraction formed by cracking naphtha and separated from the cracked products are typically listed in Table 1. The content of the hydrocarbons constituting the four specified types (A, B, C and D) of the $C_5$ fraction derived from the same source is typically set forth in Tables 2 to 5 respectively.

Table 1

| Hydrocarbons contained in the general $C_5$ fraction | Boiling point (°C) |
|---|---|
| n-pentane | 36 |
| i-pentane | 28 |
| Cyclopentane | 49 – 50 |
| Pentene-1 | 30 – 31 |
| Pentene-2 (cis) | 37 |
| Pentene-2 (trans) | 36 |
| Cyclopentene | 44 |
| 2-methyl-butene-1 | 32 |
| 3-methyl-butene-1 | 20 |
| 2-methyl-butene-2 | 38 |
| Pentadiene-1,3 | 44 |
| 2-methyl-butadiene-1,3 | 34 |
| 3-methyl-butadiene-1,2 | 34 |
| Cyclopentadiene | 41 |
| Other $C_5$ hydrocarbons | — |
| $C_3$ hydrocarbons | — |
| $C_4$ hydrocarbons | — |
| $C_6$ hydrocarbons | — |

Table 2

| Hydrocarbons contained in the $C_5$ fraction (A type) | Content (% by weight) |
|---|---|
| $C_5$ hydrocarbon | 69.4 |
| n-pentane | 16.7 |

Table 2-continued

| Hydrocarbons contained in the C₅ fraction (A type) | Content (% by weight) |
|---|---|
| i-pentane | 10.5 |
| Pentene-1, Pentene-2 (cis and trans) | 2.4 |
| Cyclopentene | 2.2 |
| 2-methyl-butene-1 | 3.7 |
| Pentadiene-1,3 | 3.1 |
| 2-methyl-butadiene-1,3 | 12.1 |
| 3-methyl-butadiene-1,2 | 6.0 |
| Cyclopentadiene | 9.4 |
| Other C₅ hydrocarbons | 3.3 |
| C₃ hydrocarbons | 0.2 |
| C₄ hydrocarbons | 5.3 |
| C₆ hydrocarbons | 17.2 |
| (dicyclopentadiene | 7.6) |
| Others | 0.3 |
| Total | 100.0 |

Table 3

| Hydrocarbons contained in the C₅ fraction (B type) | Content (% by weight) |
|---|---|
| C₅ hydrocarbons | 93.2 |
| n-pentane | 23.0 |
| i-pentane | 15.6 |
| Cyclopentane | 1.7 |
| Pentene-1 | 3.2 |
| Pentene-2 (cis and trans) | 3.7 |
| Cyclopentene | 2.2 |
| 2-methyl butene-1 | 5.5 |
| 2-methyl butene-2 | 3.5 |
| Pentadiene-1,3 | 7.8 |
| 2-methyl butadiene-1,3 | 13.0 |
| Cyclopentadiene | 9.9 |
| Other C₅ hydrocarbons | 4.1 |
| C₄ hydrocarbons | 6.8 |
| Total | 100.0 |

Table 4

| Hydrocarbons contained in the C₅ fraction (C type) | Content (% by weight) |
|---|---|
| C₅ hydrocarbons | 97.8 |
| n-pentane | 26.1 |
| i-pentane | 24.1 |
| Pentene-1, pentene-2 (cis and trans) | 4.2 |
| Cyclopentene | 1.6 |
| 2-methyl butene-1, 3-methyl butene-1 and 2-methyl butene-2 | 11.8 |
| Pentadiene-1,3 | 8.8 |
| 2-methyl butadiene-1,3 | 13.7 |
| Cyclopentadiene | 7.5 |
| C₄ hydrocarbons | 0.9 |
| C₆ hydrocarbons | 1.2 |
| Others | 0.1 |
| Total | 100.0 |

Table 5

| Hydrocarbons contained in the C₅ fraction (D type) | Content (% by weight) |
|---|---|
| C₅ hydrocarbons | 87.7 |
| n-pentane | 12.3 |
| i-pentane | 10.5 |
| Cyclopentane | 0.6 |
| Pentene-1 | 2.7 |
| Pentene-2 (cis) | 3.5 |
| Pentene-2 (trans) | 1.8 |
| Cyclopentene | 2.9 |
| 2-methyl butene-1 | 3.8 |
| 3-methyl butene-1 | 0.5 |
| 2-methyl butene-2 | 1.0 |
| Pentadiene-1,3 (trans) | 7.4 |
| Pentadiene-1,3 (cis) | 3.8 |
| 2-methyl butadiene-1,3 | 16.4 |
| Cyclopentadiene | 20.5 |
| C₃ hydrocarbons | trace |
| C₄ hydrocarbons | 10.8 |

Table 5-continued

| Hydrocarbons contained in the C₅ fraction (D type) | Content (% by weight) |
|---|---|
| C₆ hydrocarbons | trace |
| Others | 1.5 |
| Total | 100.0 |

As seen from the above list, the $C_5$ fraction contains not only cyclopentadiene but also a large number of components of relatively high reactivity such as other conjugated dienes (for example, methylbutadiene- and pentadiene-type compounds) and olefins (for example, pentene-, methylbutene- and cyclopentene-type compounds). Therefore, it was initially anticipated that reaction of acrylonitrile with the $C_5$ fraction would give rise to the noticeable growth of numerous byproducts derived from and high reactivity components, for example, adducts formed by the reaction of pentadiene-1,3 (piperylene) or 2-methyl butadiene-1,3 (isoprene) on one hand with cyclopentadiene or acrylonitrile on the other, higher molecular weight adducts formed by the reaction of said adducts with pentadienes, and various polymers of acrylonitrile, cyclopentadiene, other conjugated dienes and olefins. However, the present inventors' experiments show that where the aforesaid reaction conditions were adopted, reaction of acrylonitrile with the $C_5$ fraction itself would advantageously result in the substantially negligible formation of the above-mentioned by-products, and attain the selective production of cyanonorbornene.

The method of this invention theoretically remains unchanged whether the $C_5$ fraction of the type delivered from a naphtha cracker or the residue formed after separation from $C_5$ fraction of isoprene or other components effectively utilized as petrochemical raw materials. At any rate, it is advised to use such $C_5$ fraction as contains at least 5% by weight or preferably 7 to 40% by weight of cyclopentadiene. A smaller content of cyclopentadiene in the $C_5$ fraction than 5% by weight is not desired, because it fails smoothly to react with acrylonitrile. Further, where the content of said cyclopentadiene falls below 5% by weight, then the $C_5$ fraction naturally contains a larger amount of other components and then said reaction should be carried out under more severe conditions, leading to the noticeable formation of by-products. As the result, a larger volumes of steam has to be applied for separation of the produced cyanonorbornene from the other components of the $C_5$ fraction and the byproducts, rendering the method practically unsuitable due to decreased economies.

The $C_5$ fraction just delivered from the naphtha cracker generally contains 10 to 30% by weight of cyclopentadiene. When the $C_5$ fraction is allowed to stand for a certain length of time, said cyclopentadiene is dimerized into dicyclopentadiene. Therefore after said $C_5$ fraction is left intact, the content of cyclopentadiene therein will be reduced to 7 to 8% by weight. In contrast, the aforesaid residual $C_5$ fraction remaining after separation of, for example, isoprene, contains above 40% by weight of cyclopentadiene. Accordingly, it is generally preferred to use the $C_5$ fraction containing 7 to 40% by weight of cyclopentadiene.

An amount of acrylonitrile used for reaction with the $C_5$ fraction is chosen to be 0.3 to 3.0 mols, preferably 0.6 to 1.5 mols, or most suitably 0.8 to 1.1 mols per mol of cyclopentadiene contained in the $C_5$ fraction. If the proportion of acrylonitrile exceeds 3.0 mols per mol of cyclopentadiene, then a side reaction would become noticeable to decrease the selectivity of acrylonitrile with cyclopentadiene. Conversely where acrylonitrile is applied in a smaller amount of 0.3 mol, then a considerable amount of the $C_5$ fraction would have to be assumed to provide desired cyanonorbornene. As the result, large volumes of steam would be needed to distill out other components from the reaction product in order to separate pure cyanonorbornene, thus rendering the apparatus unnecessarily large. Both cases would undesirably decrease the economics of a method for manufacturing cyanonorbornene.

Generally, the higher the temperature applied, the quicker the reaction. However, a high temperature would conversely reduce the selectivity of acrylonitrile with cyclopentadiene. Especially, a higher temperature than 150°C would lead to the noticeable formation of high boiling components. On the other hand, reaction conducted at a low level of temperature near room temperature enables acrylonitrile to display a very prominent selectivity with cyclopentadiene, suppressing the growth of objectionable byproducts to a substantially negligible extent. It is therefore chosen to carry out reaction between acrylonitrile and the $C_5$ fraction at temperatures ranging between 0° and 150°C, or preferably 20° and 100°C.

With the cyanonorbornene-manufacturing method of this invention, reaction may be effected in the gaseous or liquid phase. Further where required, it is possible selectively to use third components other than the raw materials, such as a solvent, catalyst, polymerization inhibitor, etc.

The solvent may consist of any kind of organic solvent which does not react with the starting materials. Said organic solvent includes aliphatic hydrocarbons such as butane, pentane, hexane, heptane and octane; aromatic hydrocarbons such as benzene, toluene, and xylene; and halogenated hydrocarbons such as methylene chloride, 1,2-dichloroethane, 1,3-dichloropropane, and 1-chlorobutane. Other organic solvents include diethyl ether, tetrahydrofuran, 1,3-dioxane, ethyl acetate, isobutyl acetate, dimethyl formamide, and dimethyl sulfoxide.

Referring to the catalyst used in this invention, the group of the Lewis acid catalysts may be cited as typical. Preferred among said group are stannic chloride ($SnCl_4$), boron trifluoride ($BF_3$) and antimony trichloride ($SbCl_3$), but most preferred is aluminium trichloride ($AlCl_3$).

The polymerization inhibitor includes hydroquinone, hydroquinone monomethyl ether, hydroquinone monoethyl ether, $\alpha$-naphthol, t-butyl catechol, $\alpha$-chloranyl, benzoquinone, and diphenyl picryl hydrazyl.

With the cyanonorbornene-manufacturing method of this invention wherein one of the raw materials is constituted by the $C_5$ fraction consisting of a mixture of various kinds of hydrocarbon, it was initially anticipated that reaction of acrylonitrile with said $C_5$ fraction would lead to the formation of many by-products. However, the method of the invention has been shown only to result in the growth of very minute amounts of by-products. Namely, the method of the present invention has been proved very advantageous which utilizes the fact that acrylonitrile among typical dienophiles taking part in the ordinary Diels-Alder reaction carries out a selective or unique reaction with cyclopentadiene contained in the $C_5$ fraction under the specified conditions.

Reaction between the $C_5$ fraction and any other dienophile than acrylonitrile hardly takes place to provide the corresponding norbornene derivative, even if said reaction is effected according to the method of this invention, as obviously seen from the results of the later described controls shown in Tables 14 to 17. This fact proves that the dienophile which should be reacted with the $C_5$ fraction according to the method of the invention is limited to acrylonitrile.

There will now be described the typical concrete examples which were carried out under the specified conditions for better understanding of the invention. Obviously, the invention is not limited thereby at all.

EXAMPLE 1

A 300 ml autoclave provided with a magnetic stirrer was charged with 100 g of the $C_5$ fraction previously stored at low temperature of $-78°C$, which had a boiling point ranging from 20° to 50°C and contained 20.4% by weight of cyclopentadiene, 13 g of acrylonitrile and 100 mg of hydroquinone monomethyl ether as a polymerization inhibitor, with reaction continued for 3 hours at 20°C. Upon completion of the reaction, the mass in the autoclave was taken into a flask capable of being tightly sealed, and immediately qualitative and quantitative analyses were made of said mass by gas chromatography. After the quantitative analysis, volatile matter was distilled out at vacuum of 0.1 mm Hg and a temperature up to 200°C. In this case, any residue, if resulting, was regarded as a polymer. In Example 1, however, no polymer was detected. The composition of the raw material mixture and the experimental results are set forth in Table 6 below, the reaction selectivity of acrylonitrile with respect to cyclopentadiene being 99.8%.

Table 6

| | | Amount (g) |
|---|---|---|
| I. | Raw material mixture | |
| | Acrylonitrile (AN) | 13.0 |
| | $C_5$ fraction containing: | 100.0 |
| | Cyclopentadiene (CP) | 20.4 |
| | Isoprene | 16.4 |
| | 1,3-pentadiene | 11.1 |
| | Methylbutenes | 5.3 |
| | Pentenes | 9.5 |
| | Saturated hydrocarbons | 25.8 |
| | Others | 11.5 |
| II. | Reaction products | |
| | Cyanonorbornene | 24.25 |
| | Isoprene-AN adduct | 0.02 |
| | 1,3-pentadiene-AN adduct | 0.04 |
| | Cyanonorbornene-CP adduct | 0 |
| | Dicyclopentadiene | 3.61 |
| | Others | 0 |
| | Polymer | 0 |
| | Unreacted AN | 2.1 |

EXAMPLE 2

The reaction was carried out under substantially the same conditions as in Example 1, with the reaction temperature changed to 50°C and then the qualitative and quantitative analyses were conducted in the same manner as in Exmaple 1, the results being presented in Table 7 below. The reaction selectivity of acrylonitrile with respect to cyclopentadiene was 97.6%.

Table 7

| | Amount (g) |
|---|---|
| Raw material mixture (same as in Table 6) | |
| II. Reaction products | |
| Cyanonorbornene | 26.8 |

Table 7 -continued

| | |
|---|---|
| Isoprene-AN adduct | 0.04 |
| 1,3-pentadiene-AN adduct | 0.05 |
| Cyanonorbornene-CP adduct | 0.86 |
| Dicyclopentadiene | 3.72 |
| Others | 0 |
| Polymer | trace |
| Unreacted AN | 1.07 |

EXAMPLE 3

The reaction was conducted under substantially the same conditions as in Example 1, with the reaction temperature changed to 100°C and then the qualitative and quantitative analyses were carried out in the same manner as in Example 1, the results being shown in Table 8 below. The reaction selectivity of acrylonitrile with respect to cyclopentadiene was 91.7%. In this experiment, 6.84 g of unidentified reaction product was produced.

Table 8

| | Amount (g) |
|---|---|
| I. Raw material mixture (same as in Table 6) | |
| II. Reaction products | |
| Cyanonorbornene | 24.9 |
| Isoprene-AN adduct | 0.05 |
| 1,3-pentadiene-AN adduct | 0.06 |
| Cyanonorbornene-AN adduct | 3.39 |
| Dicyclopentadiene | 2.02 |
| Others | 6.34 |
| Polymer | 0.45 |
| Unreacted AN | 0 |

EXAMPLES 4, 5

The reaction was carried out under substantially the same conditions as in Example 2, with the amount of acrylonitrile changed as shown in Tables 9 and 10 and then the qualitative and quantitative analyses were performed in the same manner as in Example 2, the results being indicated in Tables 9 and 10 below.

Table 9

| | Amount(g) |
|---|---|
| I. Raw material mixture | |
| Acrylonitrile | 24.41 |
| C$_5$ fraction containing the same components as listed in Table 6 | 100.0 |
| II. Reaction products | |
| Cyanonorbornene | 34.78 |
| Isoprene-AN adduct | 0.18 |
| 1,3-pentadiene-AN adduct | 0.21 |
| Cyanonorbornene-CP adduct | 0.45 |
| Dicyclopentadiene | 0.74 |
| Others | 0 |
| Polymer | trace |
| Untreated CP | 0 |
| Unreacted AN | 8.49 |

Table 10

| | Amount (g) |
|---|---|
| I. Raw material mixture | |
| Acrylonitrile | 7.96 |
| C$_5$ fraction containing the same components as given in Table 6 | 100.0 |
| II. Reaction products | |
| Cyanonorbornene | 16.24 |
| Isoprene-AN adduct | 0.01 |
| 1,3-pentadiene-AN adduct | 0.02 |
| Cyanonorbornene-CP adduct | 1.12 |
| Dicyclopentadiene | 5.30 |
| Others | 0 |
| Polymer | trace |
| Unreacted AN | 0.27 |

EXAMPLES 6 to 8

Since the composition of the C$_5$ fraction is known to vary with the source petroleum fraction from which said C$_5$ fraction is derived as well as with the conditions of cracking, various kinds of hydrocarbon were mixed with each other mixture for preparation of different C$_5$ fractions having a various compositions and a boiling point ranging from 20° to 50°C. Under this condition, reaction was carried out for 3 hours at 50°C, the results being set forth in Tables 11, 12 and 13 below.

Table 11

| | Amount (g) |
|---|---|
| I. Raw material mixture | |
| Acrylonitrile | 7.23 |
| C$_5$ fraction containing | 100.0 |
| Cyclopentadiene | 10.0 |
| Isoprene | 18.0 |
| 1,3-pentadiene | 12.0 |
| 2-methyl butene-2 | 10.0 |
| Pentene-1 | 10.0 |
| n-pentane | 40.0 |
| II. Reaction products | |
| Cyanonorbornene | 13.76 |
| Isoprene-AN adduct | 0.03 |
| 1,3-pentadiene-AN adduct | 0.06 |
| Cyanonorbornene-CP adduct | 0.28 |
| Dicyclopentadiene | 1.30 |
| Others | 0 |
| Polymer | trace |
| Unreacted AN | 0.93 |

Table 12

| | Amount (g) |
|---|---|
| I. Raw material mixture | |
| Acrylonitrile | 14.45 |
| C$_5$ fraction containing | 108.0 |
| Cyclopentadiene | 20.0 |
| Isoprene | 18.0 |
| 1,3-pentadiene | 12.0 |
| 2-methyl butene-2 | 13.0 |
| Pentene-1 | 10.0 |
| n-pentane | 35.0 |
| II. Reaction products | |
| Cyanonorbornene | 28.56 |
| Isoprene-AN adduct | 0.02 |
| 1,3-pentadiene-AN adduct | 0.06 |
| Cyanonorbornene-CP adduct | 0.90 |
| Dicyclopentadiene | 2.26 |
| Others | 0 |
| Polymer | Trace |
| Unreacted AN | 1.17 |

Table 13

| | Amount (g) |
|---|---|
| I. Raw material mixture | |
| Acrylonitrile | 21.68 |
| C$_5$ fraction containing: | 100.0 |
| Cyclopentadiene | 30.0 |
| Isoprene | 18.0 |
| 1,3-pentadiene | 12.0 |
| 2-methyl butene-2 | 10.0 |
| Pentene-1 | 10.0 |
| n-pentane | 20.0 |
| II. Reaction products | |
| Cyanonorbornene | 44.74 |
| Isoprene-AN adduct | 0.01 |
| 1,3-pentadiene-AN adduct | 0.05 |
| Cyanonorbornene-CP adduct | 0.89 |
| Dicyclopentadiene | 3.24 |
| Others | 0 |
| Polymer | trace |
| Unreacted AN | 1.28 |

Controls 1 to 4

The results of reaction between the C₅ fraction and other dienophiles than acrylonitrile, namely, methyl methacrylate, allyl chloride, methylvinyl ether and trans butene-2 are presented in Tables 14, 15, 16 and 17 respectively.

Table 14

| | Amount (g) | |
|---|---|---|
| I. Raw material mixture | | |
| Methyl methacrylate (MMA) | 24.5 | |
| C₅ fraction (same as in Table 6) | 100.0 | |
| II. Products | | |
| Norbornene derivatives | trace | 2.9 |
| Isoprene-MMA adduct | — | trace |
| 1,3-pentadiene-MMA adduct | — | trace |
| Norbornene derivatives-CP adduct | — | — |
| Dicyclopentadiene | 3.5 | 3.8 |
| Others | — | — |
| Polymer | — | trace |
| Unreacted MMA | 24.3 | 22.0 |
| Unreacted CP | 16.5 | 13.8 |
| Reaction temperature-reaction time | 20°C-48 hrs | 50°C-1.5 hrs |

Table 15

| | Amount (g) |
|---|---|
| I. Raw material mixture | |
| Allylchloride (AC) | 24.6 |
| C₅ fraction (same as in Table 6) | 100.0 |
| II. Products | |
| Norbornene derivatives | trace |
| Isoprene-AC adduct | — |
| 1,3-pentadiene-AC adduct | — |
| Norbornene derivatives-CP adduct | — |
| Dicyclopentadiene | 4.1 |
| Others | — |
| Polymer | — |
| Unreacted AC | — |
| Unreacted CP | 15.7 |
| Reaction temperature-reaction time | 50°C—1.5 hrs |

Table 16

| | Amount (g) |
|---|---|
| I. Raw material mixture | |
| Methylvinyl ether (MVE) | 14.2 |
| C₅ fraction (same as in Table 6) | 100.0 |
| II. Products | |
| Norbornene derivatives | — |
| Isoprene-MVE adduct | — |
| 1,3-pentadiene-MVE adduct | — |
| Norbornene derivatives -CP adduct | — |
| Dicyclopentadiene | 4.2 |
| Others | — |
| Polymer | — |
| Unreacted MVE | 14.1 |
| Unreacted CP | 15.9 |
| Reaction temperature-reaction time | 50°C-1.5 hrs |

Table 17

| | Amount (g) |
|---|---|
| I. Raw material mixture | |
| Trans-butene-2 (TB) | 13.8 |
| C₅ fraction (same as in Table 6) | 100.0 |
| II. Products | |
| Norbornene derivatives | trace |
| Isoprene-TB adduct | — |

Table 17-continued

| | |
|---|---|
| 1,3-pentadiene-TB adduct | — |
| Norbornene derivatives-CP adduct | — |
| Dicyclopentadiene | 4.1 |
| Others | — |
| Polymer | — |
| Unreacted TB | 13.7 |
| Unreacted CP | 15.6 |
| Reaction temperature-reaction time | 1.5 hrs. |

What we claim is:

1. A method for manufacturing cyanonorbornene which comprises reacting acrylonitrile with a C₅ fraction resulting from cracking a petroleum fraction consisting essentially of a mixture of hydrocarbons predominately of 5-carbon atom hydrocarbons comprising at least 5% by weight of cyclopentadiene, said C₅ fraction having a boiling point between about 15 to 55°C, at a temperature between about 0 and 150°C, with the molar ratio of acrylonitrile to cyclopentadiene contained in said C₅ fraction being between about 0.3:1 and 3:1

2. A method for manufacturing cyanonorbornene according to claim 1, wherein the reaction is carried out in the presence of an organic solvent.

3. A method for manufacturing cyanonorbornene according to claim 1, wherein the reaction is conducted in the presence of any of the Lewis acid catalysts.

4. A method for manufacturing cyanonorbornene according to claim 1, wherein the reaction is effected in the presence of a polymerization inhibitor.

5. A method for manufacturing cyanonorbornene according to claim 1, wherein the petroleum fraction is naphtha.

6. A method for manufacturing cyanonorbornene according to claim 2, wherein the petroleum fraction is naphtha.

7. A method for manufacturing cyanonorbornene according to claim 3, wherein the petroleum fraction is naptha.

8. A method for manufacturing cyanonorbornene according to claim 4, wherein the petroleum fraction is naphtha.

9. A method for manufacturing cyanonorbornene according to claim 2, wherein the organic solvent is selected from the group consisting of butane, pentane, hexane, heptane, octane, benzene, toluene, xylene, methylene chloride, 1,2-dichloroethane, 1,3-dichloropropane, 1-chlorobutane, diethyl ether, tetrahydrofuran, 1,3-dioxane, ethyl acetate, isobutyl acetate, dimethyl formamide, and dimethyl sulfoxide.

10. A method for manufacturing cyanonorbornene according to claim 3 wherein the Lewis acid catalyst is selected from the group consisting of aluminium trichloride, stannic chloride, boron trifluoride and antimony trichloride.

11. A method for manufacturing cyanonorbornene according to claim 4, wherein the polymerization inhibitor is selected from the group consisting of hydroquinone. hydroquinone monomethyl ether, hydroquinone monoethyl ether, α-naphthol, t-butyl catechol, α-chloranyl, benzoquinone and diphenyl picryl hydrazyl.

12. A method for manufacturing cyanonorbornene according to claim 1, wherein the C₅ fraction contains 7 to 40% by weight of cyclopentadiene.

13. A method for manufacturing cyanonorbornene according to claim 1, wherein reaction is carried out at a temperature ranging from 20° to 100°C.

14. A method for manufacturing cyanonorbornene according to claim 1 wherein the molar ratio of acrylonitrile to cyclopentadiene is chosen to fall within the range from 0.6:1 to 1.5:1.

15. A method for manufacturing cyanonorbornene according to claim 1, wherein the molar ratio of acrylonitrile to cyclopentadiene is chosen to fall within the range from 0.8:1 to 1.1:1.

16. A method for manufacturing cyanonorbornene which comprises reacting acrylonitrile with a $C_5$ fraction resulting from cracking naphtha consisting essentially of 5-carbon atom hydrocarbons comprising 7 to 40% by weight cyclopentadiene, said $C_5$ fraction having a boiling point between about 15 to 55°C, at a temperature between about 20 to 100°C, with the molar ratio of acrylonitrile to cyclopentadiene contained in said $C_5$ fraction being between about 0.8:1 and 1.1:1.

\* \* \* \* \*